(12) United States Patent
Sasaki et al.

(10) Patent No.: US 12,251,578 B2
(45) Date of Patent: Mar. 18, 2025

(54) BEAM MONITORING SYSTEM, PARTICLE THERAPY SYSTEM, AND BEAM MONITORING METHOD

(71) Applicant: HITACHI, LTD., Tokyo (JP)

(72) Inventors: Kota Sasaki, Tokyo (JP); Kouichi Okada, Tokyo (JP); Yuichiro Ueno, Tokyo (JP)

(73) Assignee: HITACHI, LTD., Tokyo (JP)

( * ) Notice: Subject to any disclaimer, the term of this patent is extended or adjusted under 35 U.S.C. 154(b) by 232 days.

(21) Appl. No.: 17/797,143

(22) PCT Filed: Aug. 25, 2020

(86) PCT No.: PCT/JP2020/032027
§ 371 (c)(1),
(2) Date: Aug. 3, 2022

(87) PCT Pub. No.: WO2021/161561
PCT Pub. Date: Aug. 19, 2021

(65) Prior Publication Data
US 2023/0056147 A1   Feb. 23, 2023

(30) Foreign Application Priority Data
Feb. 14, 2020 (JP) ................. 2020-023654

(51) Int. Cl.
*A61N 5/10*   (2006.01)

(52) U.S. Cl.
CPC ......... *A61N 5/1067* (2013.01); *A61N 5/1071* (2013.01); *A61N 2005/1087* (2013.01); *A61N 2005/1094* (2013.01)

(58) Field of Classification Search
CPC ................ A61N 5/1067; A61N 5/1071; A61N 2005/1087; A61N 2005/1094
See application file for complete search history.

(56) References Cited

U.S. PATENT DOCUMENTS

| 2005/0195931 A1* | 9/2005 | Maglich ............ G01N 23/222 376/156 |
| 2007/0295910 A1* | 12/2007 | Harada ............ A61N 5/1049 250/354.1 |

(Continued)

FOREIGN PATENT DOCUMENTS

| JP | 7-148276 A | 6/1995 |
| JP | 2011-526504 A | 10/2011 |

(Continued)

OTHER PUBLICATIONS

I Perali et al., "Prompt gamma imaging of proton pencil beams at clinical dose rate", Physics in Medicine and Biology, 59, Sep. 10, 2014 pp. 5849-5871.

(Continued)

*Primary Examiner* — Blake C Riddick
(74) *Attorney, Agent, or Firm* — MATTINGLY & MALUR, PC

(57) ABSTRACT

An object of the present invention is to increase sensitivity and position resolution of measurement of an arrival position of a charged particle beam irradiated during treatment. A beam monitoring system includes: a gamma ray detector that detects gamma rays generated by interaction between a charged particle beam and an irradiation target; a shield that is disposed between the gamma ray detector and an irradiation axis of the beam and has a plurality of slits; and a calculation unit that analyzes a detection result of the gamma ray detector and reconfigures a count distribution of the detected gamma rays into a distribution of the beam irradiation axis based on a geometric arrangement of the shield, the detector, and the irradiation axis of the beam. The calculation unit obtains the arrival position of the particle beam from the reconfigured distribution.

13 Claims, 12 Drawing Sheets

(56) References Cited

U.S. PATENT DOCUMENTS

| | | | |
|---|---|---|---|
| 2008/0067401 A1* | 3/2008 | Harada | G21K 5/04 250/396 R |
| 2008/0234531 A1* | 9/2008 | Welch | A61N 5/10 600/2 |
| 2009/0314960 A1* | 12/2009 | Balakin | A61N 5/1049 250/492.3 |
| 2011/0057110 A1* | 3/2011 | Testa | G01T 1/29 250/370.07 |
| 2011/0084211 A1 | 4/2011 | Yamaya et al. | |
| 2011/0121195 A1* | 5/2011 | Harada | A61N 5/1078 250/492.3 |
| 2011/0186720 A1 | 8/2011 | Jongen et al. | |
| 2011/0248188 A1* | 10/2011 | Brusasco | A61N 5/1048 250/492.1 |
| 2012/0025076 A1* | 2/2012 | Kraft | A61N 5/1049 250/307 |
| 2012/0056098 A1* | 3/2012 | Harada | G21K 1/093 250/396 R |
| 2012/0119105 A1* | 5/2012 | Iwata | G21K 1/10 29/592 |
| 2012/0223247 A1* | 9/2012 | Honda | A61N 5/1043 250/396 R |
| 2012/0313002 A1* | 12/2012 | Ikeda | A61N 5/1043 250/492.1 |
| 2013/0046127 A1* | 2/2013 | Nagamine | G01T 1/29 600/1 |
| 2013/0053617 A1* | 2/2013 | Pu | A61N 5/1048 600/1 |
| 2014/0061493 A1* | 3/2014 | Prieels | A61N 5/1071 250/393 |
| 2014/0145088 A1* | 5/2014 | Prieels | G01T 1/2914 250/393 |
| 2015/0041665 A1* | 2/2015 | Hollebeek | G01T 1/2935 250/374 |
| 2015/0087882 A1* | 3/2015 | Pausch | G01T 1/29 600/1 |
| 2015/0297917 A1* | 10/2015 | Beekman | A61N 5/1071 250/363.01 |
| 2015/0321025 A1* | 11/2015 | Freud | A61B 6/4291 600/1 |
| 2015/0352377 A1* | 12/2015 | Kato | A61N 5/1075 600/1 |
| 2015/0379699 A1* | 12/2015 | Takeuchi | G06T 5/50 348/77 |
| 2015/0380121 A1* | 12/2015 | Beekman | G21K 1/025 378/147 |
| 2016/0114189 A1* | 4/2016 | Mihailescu | A61N 5/1045 600/1 |
| 2017/0056688 A1* | 3/2017 | Penfold | A61N 5/1049 |
| 2017/0120077 A1* | 5/2017 | Allinson | A61B 6/032 |
| 2017/0281977 A1* | 10/2017 | Beekman | A61N 5/1067 |
| 2018/0015304 A1* | 1/2018 | Ohishi | A61N 5/1049 |
| 2018/0099154 A1* | 4/2018 | Prieels | A61N 5/1064 |
| 2018/0117360 A1* | 5/2018 | Kuwahara | G21K 1/08 |
| 2018/0154183 A1* | 6/2018 | Sahadevan | A61M 1/3615 |
| 2018/0236265 A1 | 8/2018 | Mukawa et al. | |
| 2019/0111281 A1* | 4/2019 | Wulff | G16H 70/20 |
| 2019/0175950 A1* | 6/2019 | Nagumo | G01T 1/2023 |
| 2019/0184197 A1* | 6/2019 | Fallone | A61N 5/1071 |
| 2020/0298024 A1* | 9/2020 | Lee | G01T 1/20181 |
| 2020/0316404 A1* | 10/2020 | Seco | G01T 1/201 |
| 2021/0286095 A1* | 9/2021 | Sauli | G01T 1/2023 |
| 2022/0161061 A1* | 5/2022 | Meric | A61N 5/1071 |
| 2022/0249872 A1* | 8/2022 | Seco | A61N 5/1081 |
| 2023/0146548 A1* | 5/2023 | Palm | G01T 1/2914 250/252.1 |

FOREIGN PATENT DOCUMENTS

| | | |
|---|---|---|
| JP | 2015-188589 A | 11/2015 |
| JP | 2017-80161 A | 5/2017 |
| JP | 2019-088597 A | 6/2019 |
| KR | 10-2010-0133240 A | 12/2010 |
| WO | 2010/013345 A1 | 2/2010 |

OTHER PUBLICATIONS

International Search Report of PCT/JP2020/032027 dated Oct. 27, 2020.

* cited by examiner

BEAM MONITORING SYSTEM, PARTICLE THERAPY SYSTEM, AND BEAM MONITORING METHOD

TECHNICAL FIELD

The present invention relates to a particle therapy system, and particularly to a technique for measuring a range of a particle beam in a body when a tumor is irradiated with a particle beam.

BACKGROUND ART

In the particle therapy, a tumor of a patient is treated by irradiating the tumor with a particle beam of protons, carbon, or the like. In particle therapy, a particle beam is generated by accelerating a particle by a particle beam generator, is guided to a treatment room by a beam transport system, and is emitted from an irradiation nozzle in the treatment room toward a treatment site of a patient. In general, a charged particle beam (hereinafter, simply referred to as a particle beam) such as a proton beam or a heavy particle beam with which the body of a patient is irradiated has a property of stopping at a predetermined depth and maximizing energy immediately before that. The depth that the particle beam reaches is determined according to the energy of the particle beam.

In the particle therapy, by taking advantage of the property of the particle beam, the arrival position of the particle beam is adjusted by changing the energy of the particle beam, the particle beam is stopped at the target volume, and immediately before that, the energy is applied to the target volume to destroy the tissue of the target volume. However, the actual arrival position of the particle beam does not necessarily coincide with the designed arrival position due to a factor on the apparatus side or a factor on the patient side. Therefore, in the treatment, it is necessary to confirm the arrival position of the particle beam. In order to confirm the arrival position of the particle beam, a technique for measuring a dose distribution in a depth direction (irradiation axis direction) of charged particles has been conventionally proposed.

For example, PTL 1 and NPL 1 describe an apparatus that measures a dose distribution in a depth direction by measuring radiation generated by interaction between a particle beam and an irradiation target. That is, when the particle beam travels inside the irradiation target, immediate gamma rays are generated by collision between the particle beam and atoms inside the irradiation target. In the method described in PTL 1, a gamma ray pinhole camera is used, and in the method described in NPL 1, a gamma camera using a collimator is used to measure a dose distribution in a depth direction of an immediate gamma ray generated by irradiation of a particle beam, and determine a position of a Bragg peak. Here, the Bragg peak is defined as a peak of a dose distribution when the energy of the charged particle beam is represented by the dose distribution in the depth direction. The position of the Bragg peak corresponds to the arrival position of the charged particle beam.

CITATION LIST

Patent Literature

PTL 1: JP 2011-526504 W

Non-Patent Literature

NPL 1: I. Perali, et. al., Prompt gamma imaging of proton pencil beams at clinical dose rate, Physics in Medicine and Biology 59 (19) (2014) 5849.

SUMMARY OF INVENTION

Technical Problem

In the conventional particle beam system, it is difficult to measure the position irradiated with the charged particle beam with sufficient sensitivity and resolution. For example, in the technique described in NPL 1, when the width of the gap (slit) between the collimators is increased, the sensitivity to the immediate gamma rays is improved, but there is a problem that the resolution of the position irradiated with the charged particle beam is reduced.

An object of the present invention is to improve measurement sensitivity and spatial resolution of measurement when measuring a position irradiated with a charged particle beam.

Solution to Problem

In order to achieve the above object, in the present invention, a gamma ray detector in which a plurality of detection elements are disposed is disposed along a traveling direction of a particle beam, that is, an irradiation axis, and a shield in which a plurality of transmission portions of the gamma ray are provided along the traveling direction of the beam is disposed between the irradiation axis and the gamma ray detector. Then, the generation position of the gamma ray at which the particle beam energy is maximized is estimated from the count value distribution (profile) along the irradiation axis direction of the gamma ray passing through the plurality of transmission portions and reaching each detection element of the detector.

That is, a beam monitoring system of the present invention is a beam monitoring system that detects an immediate gamma ray generated along an irradiation axis of a particle beam with which an irradiated object is irradiated and monitors a range of the particle beam, the beam monitoring system comprising: a detector including a plurality of detection elements arranged along a traveling direction of the particle beam and configured to detect gamma rays; a gamma ray shield disposed between an irradiation axis of the particle beam and the detector and formed with a transmission portion configured to transmit gamma rays; and a calculation unit configured to estimate a Bragg peak at which energy of the particle beam is maximized using a count value of the gamma rays respectively detected by the plurality of detection elements. The gamma ray shield includes a plurality of the transmission portions along the irradiation axis. The calculation unit integrates a count value of gamma rays injected at different times through the plurality of transmission portions into one detection element, creates a profile obtained by plotting an integrated value of gamma ray count values for the respective detection elements, and estimates the Bragg peak using the created profile.

A particle therapy system according to the present invention includes a particle irradiation apparatus that emits a particle beam, a control apparatus that controls the particle irradiation apparatus, and a beam monitoring apparatus that is disposed at least at one location around an irradiated object irradiated with the particle beam and monitors a range of the beam. The beam monitoring apparatus is the beam monitoring system of the present invention described above.

A beam monitoring method of the present invention is a beam monitoring method for detecting an immediate gamma ray generated along an irradiation axis of a particle beam with which an irradiated object is irradiated and monitoring a range of the particle beam, the beam monitoring method including the following steps. A detector including a plurality of detection elements that detect gamma rays is disposed in a vicinity of the irradiated object such that an arrangement direction of the detection elements substantially coincides with the irradiation axis, and a gamma ray shield in which a plurality of transmission portions that transmit the gamma rays are formed along the irradiation axis is disposed between the particle beam and the detector. When the particle beam passes through the irradiated object, count values of gamma rays injected on individual detection elements are integrated at different times through the plurality of transmission portions. A profile in which an integrated value of gamma ray count values is plotted for the respective detection elements is created, and a Bragg peak is estimated using the created profile.

Advantageous Effects of Invention

According to the present invention, by disposing the shield having the plurality of transmission portions between the irradiation axis and the gamma ray detector, the gamma ray generated along the progress of the particle beam is detected by the plurality of detectors at different generation positions through the plurality of transmission portions. According to the present invention, by analyzing the integrated value of the counting values of the gamma rays that have reached the respective detection elements from the plurality of transmission portions, it is possible to improve sensitivity and position resolution when measuring the position irradiated with the charged particle beam. As a result, the irradiation position of the particle beam can be confirmed with high accuracy, and the application site of the particle therapy can be expanded and the treatment efficiency can be improved.

DESCRIPTION OF EMBODIMENTS

Figure 1:
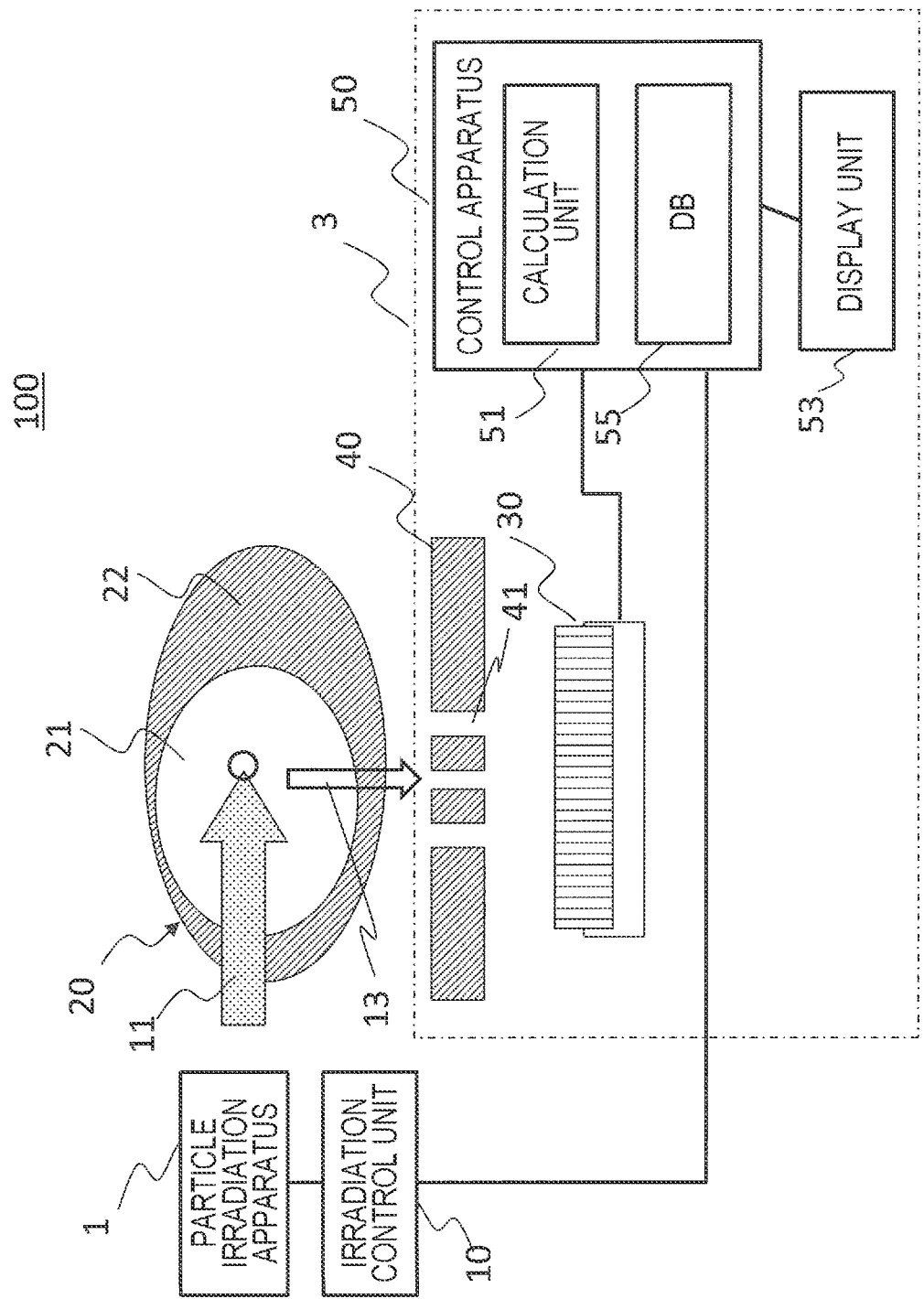
FIG. 1 is a configuration diagram illustrating an embodiment of a particle therapy system of the present invention.

Hereinafter, embodiments of the present invention will be described using the drawings. The same elements illustrated in the plurality of drawings are denoted by the same reference numerals, and redundant description will be omitted.

First, an overall configuration of a particle therapy system common to each embodiment will be described with reference to FIGS. 1 and 2.

As illustrated in FIG. 1, the particle therapy system 100 of the present embodiment includes a particle irradiation apparatus 1 that irradiates an irradiated object 20 (a patient to be subjected to particle therapy) with a particle beam and a beam monitoring apparatus 3 that monitors the particle beam irradiated to the irradiated object 20. The beam monitoring apparatus 3 includes a gamma ray detector 30 that detects an immediate gamma ray generated by irradiation with a particle beam, a gamma ray shield (hereinafter, simply referred to as a shield) 40 disposed between the gamma ray detector 30 and the irradiated object 20, and a control apparatus 50 that is connected to the gamma ray detector 30, performs an operation on the detection result, and controls the particle irradiation apparatus 1. In the present specification, a beam monitoring system incorporated in a particle therapy system is referred to as a beam monitoring apparatus.

The particle irradiation apparatus 1 irradiates the irradiated object 20 with a charged particle beam (hereinafter, simply referred to as a particle beam) 11, and includes, although not illustrated, a particle beam generator that has a cyclone, a synchrotron, or the like and generates a charged particle beam of protons, carbon, or the like, a particle beam transfer that transports the charged particle beam output from the particle beam generator, an irradiation section that controls directivity and a spot size (radiation field) of the particle beam and irradiates a target, for example, a tumor in the irradiated object 20 with the particle beam, and the like. The particle irradiation apparatus 1 may further include an irradiation control unit 10 that controls the operation of the particle beam generator and the irradiation nozzle according to the monitoring result of the beam monitoring system 3.

The gamma ray detector 30 detects an immediate gamma ray 13 generated by the body tissue of the irradiated object 20 irradiated with a particle beam 11. Immediate gamma rays are detected as count values of unit gamma rays. The gamma ray detector 30 can employ a known means as a means for detecting gamma rays, and can include, but is not limited to, a scintillator and a photoelectric converter that converts light emitted from the scintillator into an electronic signal, for example. As the scintillator, for example, $LaBr_3$, GSO, LYSO, BGO, or the like may be used, or a radiation emitting element having a composition different from these may be used. As the photoelectric converter, for example, a photoelectron multiplier, a photodiode, or the like can be used. In addition, instead of the scintillator, for example, a semiconductor detector such as CdTe or CZ may be used, and in this case, the gamma ray detector 30 uses a preamplifier instead of the photoelectric converter.

The gamma ray detector 30 is an array type detector in which a plurality of detection elements are arranged in at least a one-dimensional direction, and is disposed such that an arrangement direction of the detection elements substantially coincides with an irradiation axis of the particle beam (hereinafter, simply referred to as an irradiation axis). As a result, it is possible to capture immediate gamma rays flying at an angle with respect to the irradiation axis. The position in the irradiation axis direction is set such that the target position of irradiation set in the treatment planning is included in the detection range.

Although described in detail in an embodiment to be described later, the number of gamma ray detectors 30 may be one, but it is desirable that a plurality of gamma ray detectors are disposed around the irradiation axis. This makes it possible to enhance the accuracy of gamma ray detection. A gamma ray count value detected by each detection element of the gamma ray detector 30 is input to the control apparatus 50.

The shield 40 is formed of a material that does not substantially transmit gamma rays. As the material that does not substantially permeate, a substance having a large mass number and a high density can be used, and for example, lead or a material containing lead, tungsten, or the like may be used. The shield 40 is installed on the irradiation axis side of the gamma ray detector 30, and limits the detection range of the gamma ray detector 30. The shield 40 has a plurality of gamma ray transmission portions along the irradiation axis. The transmission portion may be a material that transmits gamma rays or a slit 41 formed in the shield 40. Hereinafter, a description will be given on the assumption that the transmission portion is a slit.

The number of slits 41 is not particularly limited as long as it is 2 or more, but is, for example, about 2 to 10. The narrower the width of the slit 41 in the irradiation axis direction, the higher the position detection accuracy but the narrower the detectable range. In addition, regarding the interval between the adjacent slits 41, ranges in which the gamma rays transmitted through the adjacent slits 41 arrive at the detector 30 preferably overlap to some extent. For example, the slit width is about 1 mm to 10 mm, and the slit interval is about 1 cm to 3 cm. However, these numerical values are merely examples, and are not limited.

By arranging the shield 40 having the plurality of transmission portions between the gamma ray generation source and the gamma ray detector 30 along the irradiation axis of the particle beam in this manner, the gamma rays from different slits 41 fly to each detection element of the gamma ray detector 30 with a time difference as the particle beam moves. Therefore, the detection output of the gamma ray detector 30 is an integrated value of the count values flying to the respective detection elements through the different slits 41. Here, a plot of the integrated value of the detector along the detection element arrangement direction (detector axis) of the detector is defined as a profile of the count value or simply a profile. Since this profile reflects the dose distribution of the particle beam, the dose distribution of the particle beam can be estimated by analyzing this.

The control apparatus 50 analyzes the detection output (profile) of the gamma ray detector 30, and estimates a point where the dose is maximized in the dose distribution in the irradiation axis direction of the particle beam, that is, a Bragg peak (BP). Therefore, the control apparatus 50 includes a calculation unit 51 that analyzes the detection output of the gamma ray detector 30. Further, the control apparatus 50 may include a display unit 53 that displays a calculation result, and a database (DB) 55 that stores data necessary for analysis, an analysis result by the calculation unit 51, and the like. A specific method of analysis performed by the calculation unit 51 will be described in detail in an embodiment to be described later.

The control apparatus 50 (calculation unit 51) can be configured by a computer or the like including a processor such as a central processing unit (CPU) or a graphics processing unit (GPU) and a memory, and the CPU reads and executes a program stored in the memory, thereby implementing the function of the calculation unit 51 by software. However, some or all of the functions of the calculation unit 51 can be implemented by hardware. For example, the calculation unit 51 may be configured using a custom IC such as an application specific integrated circuit (ASIC) or a programmable IC such as a field-programmable gate array (FPGA), and the circuit design may be performed to realize the function.

For example, a RAM, a ROM, a hard disk, a USB memory, an SD card, or the like may be used as the DB 55 included in the control apparatus 50. The DB 55 may be a storage on a communication line such as the Internet. Further, some of the processes executed by the control apparatus 50 may be executed by an external computer.

In the particle therapy system of the present embodiment, when the position of the irradiation target (tumor or the like) is determined in the treatment planning, the energy of the particle beam is set such that the position BP of the Bragg peak at which the dose distribution along the irradiation axis direction of the particle beam becomes maximum coincides with the target position of the irradiation in the target volume. Normally, the irradiation of the particle beam is performed by dividing the irradiation target into a plurality of small regions and irradiating each small region in a spot shape while changing the irradiation position. In this case, for example, the position of the small region located farthest in the irradiation axis direction is set as the irradiation target position.

Figure 2:
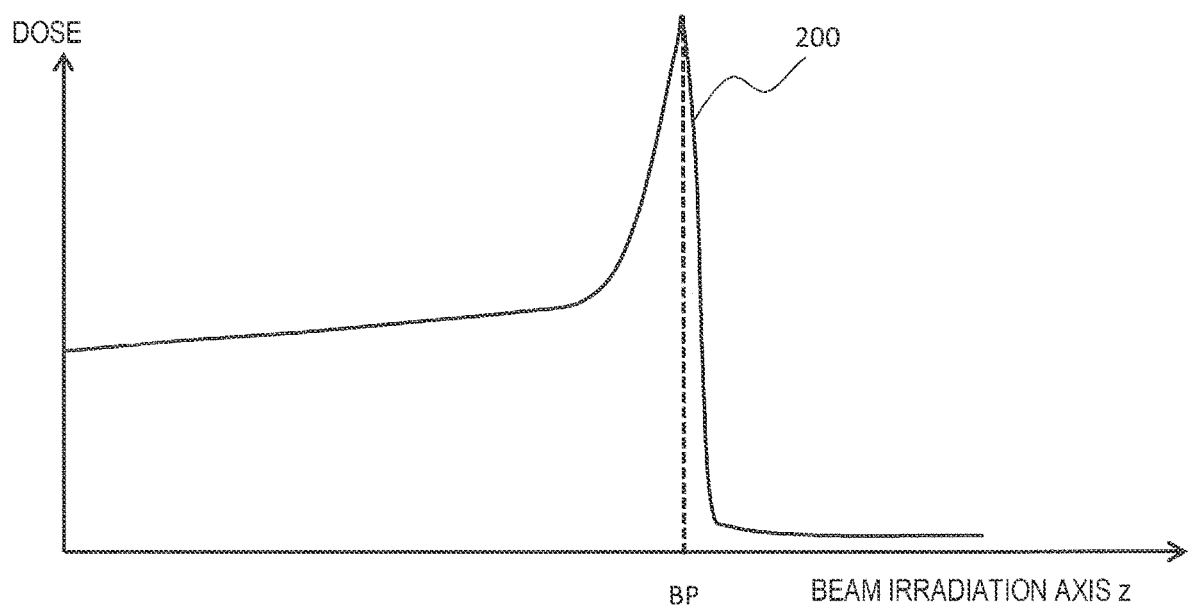
FIG. 2 is a diagram conceptually illustrating a dose distribution in a beam irradiation axis z direction.

FIG. 2 conceptually illustrates a dose distribution 200 along the irradiation axis direction of the particle beam. This distribution is obtained by associating the dose with each position in the beam irradiation axis direction z when the irradiation position of the charged particle beam calculated by the treatment planning is irradiated with the beam only once. The dose distribution of the beam irradiation axis z is maximized at a position corresponding to the energy of the particle beam. The position BP where the dose distribution becomes maximum is a position defined as a Bragg peak.

Next, the particle irradiation apparatus 1 irradiates the target position with the particle beam. At the start of irradiation with the particle beam, the beam monitoring apparatus 3 starts detection of immediate gamma rays, analyzes a distribution (profile) of the integrated value of gamma ray count values detected by the gamma ray detector 30, and calculates the position of this black peak, that is, the arrival position of charged particles. The calculated arrival position of the particle is stored in the storage device or the DB 55 in the control apparatus 50 or displayed on the display unit 53. The user can confirm whether the particle beam 11 has reached the target position of irradiation on the basis of the information displayed on the display unit 53.

When the control apparatus 50 determines that the particle beam 11 does not hit a target area 21, the control apparatus 50 sends a control signal to the particle irradiation apparatus 1 and stops the irradiation of the particle beam. Then, for example, adjustment is performed to change the target position. Alternatively, the particle irradiation apparatus 1 may be configured to perform control to correct the position where the particle beam 11 is irradiated to the irradiated object 20 via the irradiation control unit 10. Further, an instruction/suggestion to change the arrangement position of the gamma ray detector 30 may be given to the user via the display unit 53 as necessary.

According to the present embodiment, it is possible to reduce the possibility of irradiating the normal tissue located outside the target area 21 such as a tumor with the particle beam 11. As a result, even in a case where a tumor exists in the vicinity of a normal tissue 22 that is likely to be seriously damaged by irradiation with the particle beam 11, the possibility that the particle therapy can be applied can be increased.

In addition, according to the particle therapy system of the present embodiment, it is possible to confirm that the target area 21 such as a tumor is irradiated with the particle beam 11, and thus, it is possible to set the intensity of the particle beam 11 to be large and to improve the treatment efficiency.

Next, an embodiment of a beam monitoring apparatus (beam monitoring system) using a profile of gamma rays which is a detection result of the gamma ray detector 30 will be described.

First Embodiment

Figure 3:
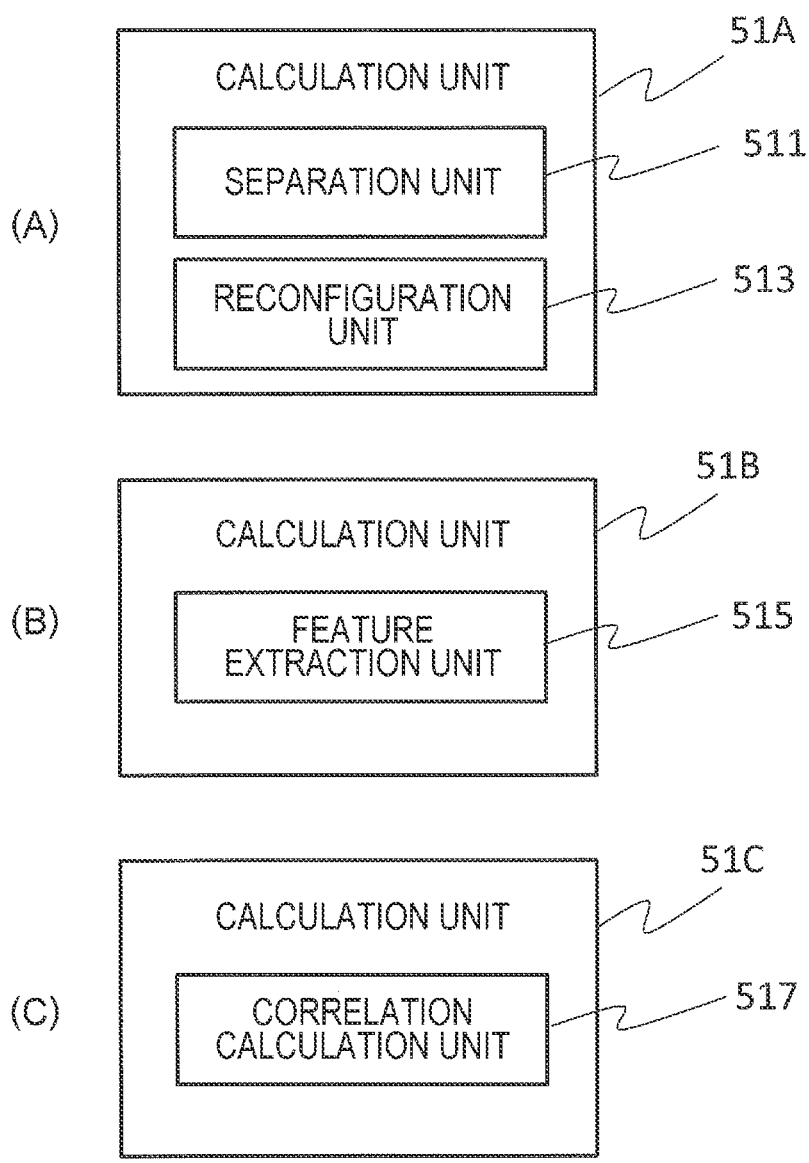
FIGS. 3(A) to 3(C) are functional block diagrams of a calculation unit of each embodiment.

The present embodiment is characterized in that the calculation unit 51 performs a reconfiguration operation using the profile to reconfigure the distribution of the gamma rays along the irradiation axis of the particle beam, and estimates the arrival position on the basis of the reconfiguration profile. Therefore, as illustrated in FIG. 3(A), the calculation unit 51A of the present embodiment includes a separation unit 511 that separates the profile for each slit and a reconfiguration unit 513 that performs a profile reconfiguration operation.

Figure 4:
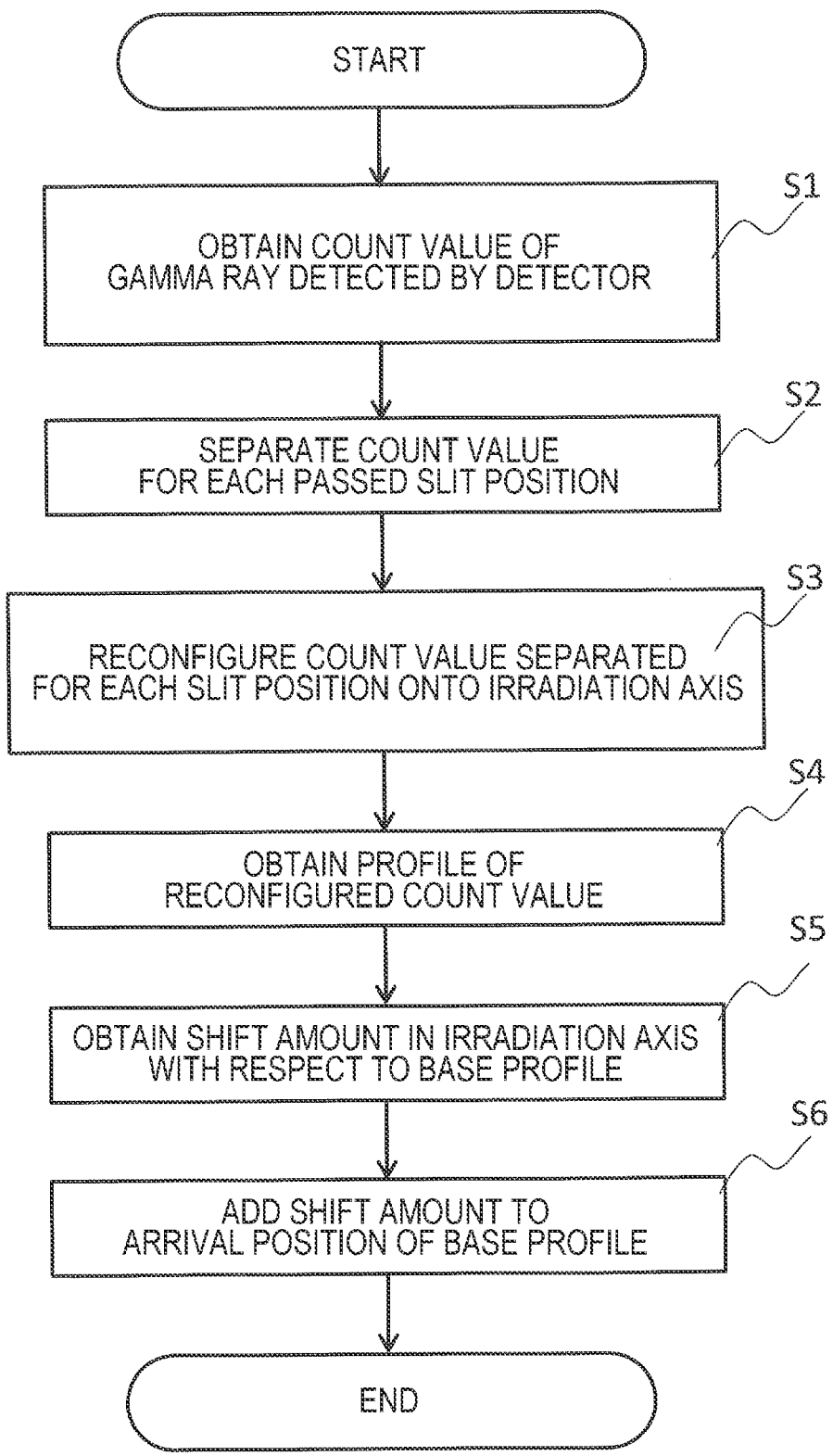
FIG. 4 is a flowchart of processing executed by a control apparatus according to a first embodiment of the present invention.

Hereinafter, processing of a calculation unit 51A of the present embodiment will be described with reference to the flow of FIG. 4 and FIG. 5. Here, processing in a case where a target position of one irradiation is irradiated with a particle beam a plurality of times (N times) will be described.

First, the gamma ray detector 30 is installed at a predetermined position in the treatment planning. For each irradiation target position, positions x=x1 to xN of the detection element on the detector axis x parallel to the beam irradiation axis are determined in advance and stored in the DB 55. In addition, a profile in a case where the gamma ray 13 generated from the particle beam 11 irradiated to the position z0 on the specific beam irradiation axis is detected is stored in the DB 55 as base data. Such base data can be obtained, for example, by detecting gamma rays generated when the particle beam 11 is irradiated by the gamma ray detector 30 using a phantom or the like for maintenance inspection or the like of the apparatus and converting a profile of the count value at that time into a profile (base reconfiguration profile) along the irradiation axis direction. The method of converting the profile of the count value into the profile along the irradiation axis direction is similar to the reconfiguration step described later, and will be described in detail in the same step.

[Calculation of Count Value and Creation of Profile: S1]

The gamma ray detector 30 detects the gamma ray 13 arriving at itself, and outputs a detection signal indicating that the gamma ray 13 is detected to the control apparatus 50. The calculation unit 51A obtains a count value of the gamma rays 13 based on the detection signal output from each detection element of the gamma ray detector 30 (S1).

The count value represents the frequency at which gamma rays are detected in N times of irradiation. That is, a histogram of the gamma ray energy detected until the end of N times of irradiation is created, and the gamma ray energy in a predetermined energy range is counted as a count value.

Figure 5:
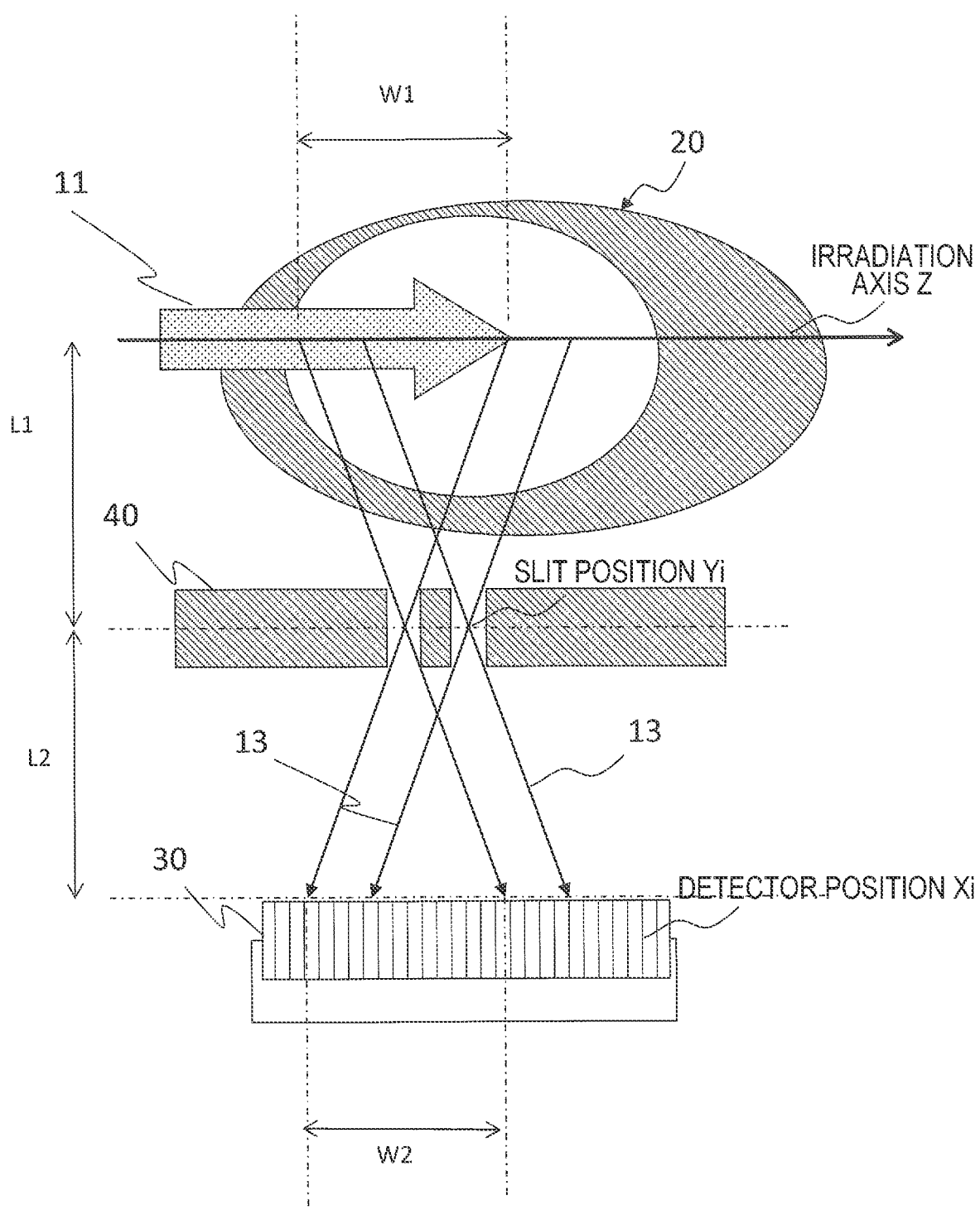
FIG. 5 is a conceptual diagram illustrating a detector and a shield structure according to the first embodiment of the present invention.

FIG. 5 is a schematic diagram illustrating a relationship between the gamma ray detector 30 and the shield 40 when the target position of irradiation is irradiated with the particle beam 11. In the drawing, the gamma ray 13 that has arrived at the gamma ray detector 30 from the irradiation axis of the particle beam along the energy applied to a body tissue by the charged particle beam 11 is schematically illustrated.

As illustrated in FIG. 5, the gamma ray 13 having passed through the plurality of slits 41 disposed in parallel with the gamma ray detector 30 is detected at a position xi of the detection element at a position inverted from the irradiation axis with a slit position Yi as the center. At this time, the arrival direction of the gamma ray 13 having passed through the slit 41 with respect to the position x of the gamma ray detector is determined based on the geometric arrangement of the position z, the slit position Yi, and the detector position xi on the irradiation axis regardless of the arrival position of the particle beam 11. Specifically, from a thickness D of the shield 40, a width d of the slit, a distance L1 between the shield 40 and the beam irradiation axis, and a distance L2 between the gamma ray detector 30 and the shield 40, a range W1 on the beam irradiation axis where the gamma ray passing through the slit is generated, and a range W2 of the gamma ray detector 30 where the gamma ray passing through the slit arrives are determined, and the position on the irradiation axis and the position of the gamma ray detector 30 corresponding to each other are determined. However, although not illustrated, the gamma ray 13 may arrive at the gamma ray detector 30 without being shielded by the shield 40. Therefore, the spatial distribution of the gamma rays 13 measured by the gamma ray detector 30 does not coincide with the spatial distribution of the gamma rays 13 generated on the irradiation axis.

Since the shield 40 has the plurality of slits 41, when attention is paid to one detection element, the gamma rays 13 arriving at the detection element pass through the slits and arrive, so that the number of arriving gamma rays increases. At this time, the count value of the gamma rays detected by the detection element is the sum of the gamma rays that have passed through the slits and arrived.

Figure 6:
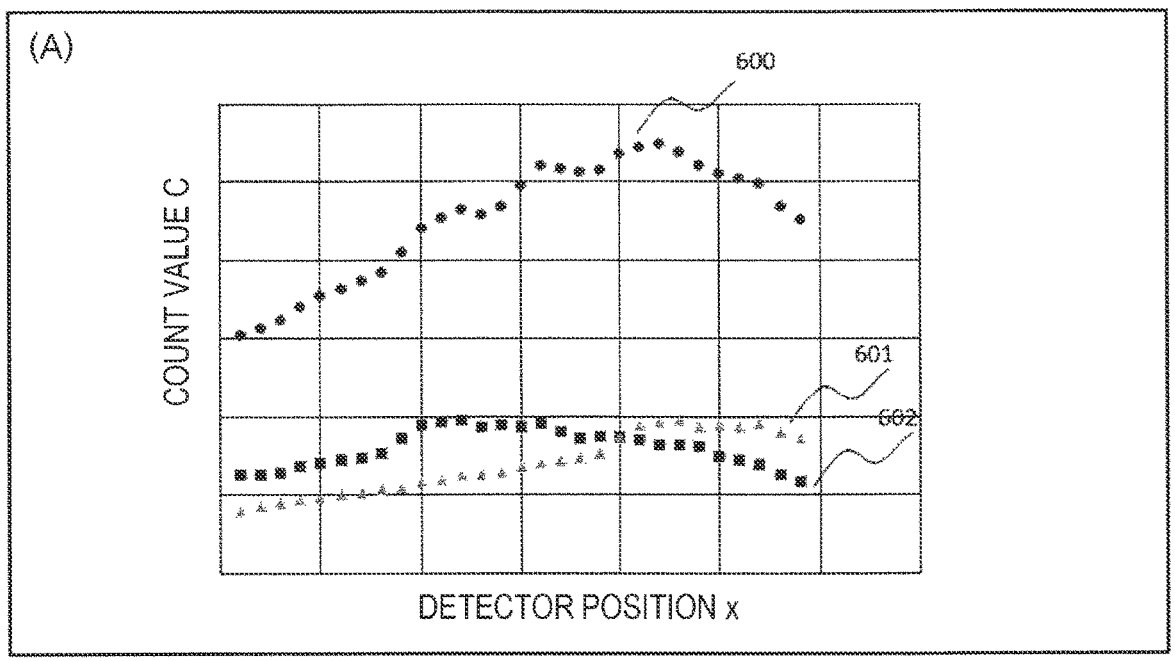
FIG. 6(A) is a conceptual diagram illustrating a count profile in the detector according to the first embodiment of the present invention.
FIG. 6(B) is a conceptual diagram illustrating a profile reconfigured to the beam irradiation axis.
Figure 6:
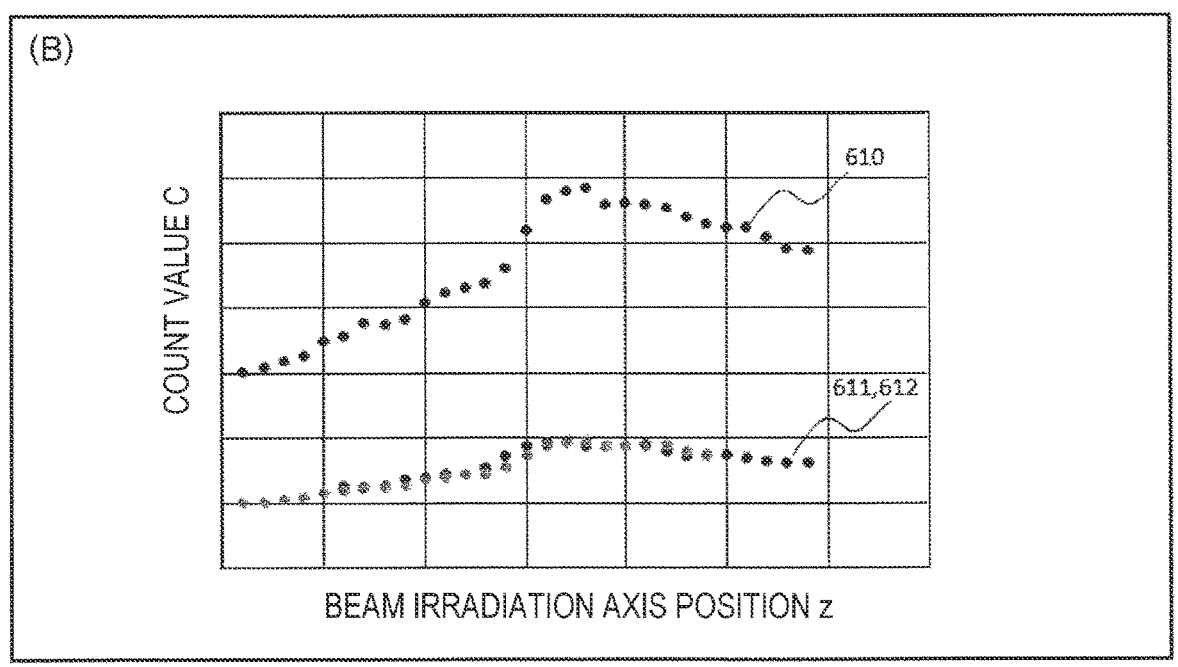

FIG. 6(A) shows a count profile 600 detected at each position (detection element) x of the gamma ray detector 30. The profile of the count value measured by the gamma ray detector 30 has a high count at a position passing through the slit 41 and a low count at a position passing through the shield 40. The count value (Ci) detected at the detector position Xi after passing through two slit positions Y1 and Y2 is the superposition of profiles 601 and 602 of the count value detected after passing through the slit position Y1 and the count value detected after passing through the slit position Y2.

[Separation for Each Slit Position: S2]

The separation unit 511 of the calculation unit 51A uses the profile 600 of the count value of the gamma ray detector 30 to separate into the profiles 601 and 602 for each slit position. As a method of separating for each slit position, for example, there is the following method. In one method, a profile at the time of passing through a single slit is obtained in advance by simulation, and this is used as a reference profile. Based on the geometric arrangement of the slit, the position of the reference profile is shifted and the reference profiles before and after the shift are added to create a composite profile. A ratio of the reference profile (count value) at each slit position in the composite profile is obtained by comparing the composite profile with a reference file at each position. This ratio is applied to the profile obtained in Step S1 to obtain the profiles 601 and 602. Although the profiles of the two slits are illustrated in FIG. 6(A), the ratio can be similarly obtained even when the number of slits is three or more.

As another method, simulation may be performed in a system having a plurality of slits, and a ratio at which gamma rays having passed through each slit are detected at each detector position xi may be obtained and separation is performed. However, the separation method described herein is merely an example in describing the present embodiment, and does not limit the present application.

[Reconfiguration: S3, S4]

The reconfiguration unit 513 of the calculation unit 51A converts (reconfigures) the profile (the profile of the count value with the detector position on the horizontal axis) for each slit position into the count value of the beam irradiation axis (S3). As described above, the gamma ray generation position on the irradiation axis and the detector position for detecting the gamma ray can be unambiguously obtained from the geometric arrangement. Therefore, the reconfiguration can be performed by setting the count value of the predetermined detector position in the created profile as the count value of the position on the irradiation axis corresponding thereto. Thereafter, the count value distributions in the beam irradiation axis for each slit position are added together to create a profile (reconfiguration profile) reconfigured for the beam irradiation axis (S4).

FIG. 6(B) illustrates a profile 610 of the count value reconfigured on the beam irradiation axis. In the drawing, on the lower side, two profiles 611 and 612 (in the drawing, both are overlapped and cannot be identified) before addition are illustrated.

[Calculation of Shift Amount and Arrival Position: S5, S6]

The calculation unit 51A reads, from the DB 55, the base data, that is, the base reconfiguration profile (profile obtained by reconfiguring the profile of the count value detected by the detector) of the gamma ray 13 generated from the charged particle beam 11 with which the position z0 on the specific beam irradiation axis is irradiated, and obtains the position BP of the Bragg peak from the positional relationship between the reconfiguration profile 610 created in Step S4 and the base data. Specifically, a shift amount Δz in the beam irradiation axis direction of the base reconfiguration profile and the reconfigured profile 610 is obtained (S5), and BP=z0+Δz, that is, the arrival position of the charged particle beam 11 is obtained (S6). The processing of obtaining the position BP of the Bragg peak based on the difference between the position of the base data and the position of the profile 610 can be performed by, for example, numerical calculation based on a program such as known image matching processing. Therefore, the processing is quickly performed by the control apparatus (calculation unit 51A).

Note that the method of calculating the beam arrival position is not limited to the above-described method. As described above, the detected profile 610 has positional information of the generated gamma rays. Since the amount of generated gamma rays is maximum at the BP position, the maximum position of the reconfiguration profile has information of the BP position. In this manner, the beam arrival position may be obtained from the maximum position of the profile 610 without using the base data.

The control apparatus 50 causes the display unit 53 to display the arrival position of the charged particle beam 11 thus obtained. By confirming the arrival position displayed on the display unit 53, the user can confirm whether the treatment is appropriately performed or adjust the particle irradiation apparatus 1 so that the actual arrival position becomes the target position before performing irradiation while changing the irradiation position.

As described above, in the particle therapy system according to the present embodiment, the gamma rays passing through the shield having the plurality of slits are detected, the gamma rays passing through each slit are separated from the geometric positional relationship among the particle charged beam, the slit, and the detector, and the profile thereof is reconfigured onto the irradiation axis, whereby the position BP of the Bragg peak is obtained with sufficient resolution, and the position irradiated with the charged particle beam (the arrival position of the charged particle beam) is obtained with sufficient resolution. As a result, in a case where the position of a tumor is at a position different from the position of the treatment planning due to a change in the posture of the patient during irradiation, a change in the body shape of the patient, or the like, the irradiation position of the particle beam can be changed, or the irradiation of the particle beam can be stopped. Therefore, even in a case where an organ having high radiosensitivity exists in the vicinity of a tumor, the possibility of applying particle therapy can be increased.

In addition, in the particle therapy system of the present embodiment, it is possible to prevent the irradiation of particle beam to a portion other than a tumor, so that it is possible to increase the irradiation amount of particle beam to the tumor in one treatment, and it is expected to improve the treatment efficiency.

Second Embodiment

In the first embodiment, the calculation unit 51A separates the profiles obtained from the detection result of the gamma ray detector 30 into profiles for each slit, and reconstructs the profiles into the profiles of the beam irradiation axis to create the reconfiguration profile, but in the present embodiment, the BP is calculated from the features of the profiles as the detection result without separating or reconfiguring the profiles as in the first embodiment. Therefore, a calculation unit 51B of the present embodiment includes a feature extraction unit 515 as illustrated in FIG. 3(B).

Figure 7:
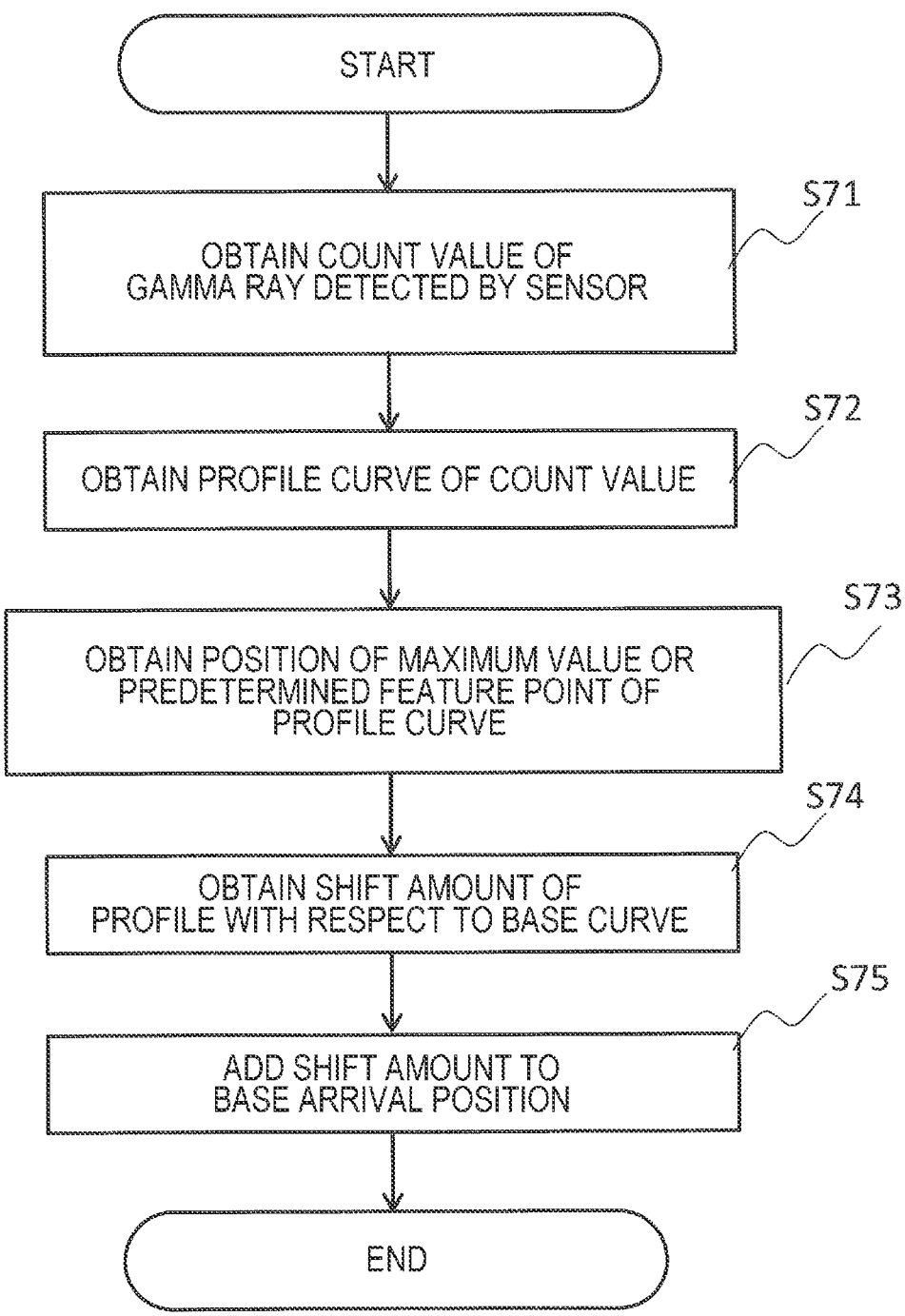
FIG. 7 is a flowchart of processing of obtaining an arrival position of a beam according to a second embodiment of the present invention.

The processing of the calculation unit 51B of the present embodiment will be described with reference to the flow of FIG. 7. Also in the present embodiment, after the gamma ray detector 30 is installed, the positions x=x1 to xN of the detection elements on the detector axis x parallel to the beam irradiation axis are determined in advance with respect to the target position of each irradiation, and are stored in the DB 55, which is the same as in the first embodiment. In the present embodiment, as the base data, a profile (base profile: count value distribution in the detection position direction) when the gamma ray detector 30 detects the gamma ray 13 generated from the charged particle beam 11 with which the position z0 on the specific beam irradiation axis is irradiated is stored in the DB 55.

[Creation of Count Profile: S71, S72]

In this step, similarly to the first embodiment, a profile is created using the count value for each detector position of the gamma ray detector 30.

[Calculation of Position and Shift Amount of Feature Point: S73, S74]

The feature extraction unit 515 obtains a feature point for the profile created in Step S72 and obtains a position thereof. As the feature point, a maximum value of the profile, a steepest position obtained from a curve obtained by differentiating the profile, and the like can be used. This position may be a position on the detector axis, or may be obtained as a difference from a predetermined point (for example, the end portion) of the detector as an origin. Similarly, for the base profile stored in the DB 55, the position of the same feature point is obtained (S73).

The shift amount ($\Delta x$) of the position of the feature point of the profile in Step S72 with respect to the position of the feature point of the base profile is calculated (S74).

[Calculation of BP Position: S75]

The calculation unit 51B converts the shift amount ($\Delta x$) in the detector axis direction calculated in Step S74 into the shift amount ($\Delta z$) on the irradiation axis based on the geometric arrangement relationship with the detector 30, the slit 41 of the shield 40, and the irradiation axis, and adds the converted shift amount to the irradiation position (z0) of the base data to obtain the arrival position of the charged particle beam 11.

Figure 8:
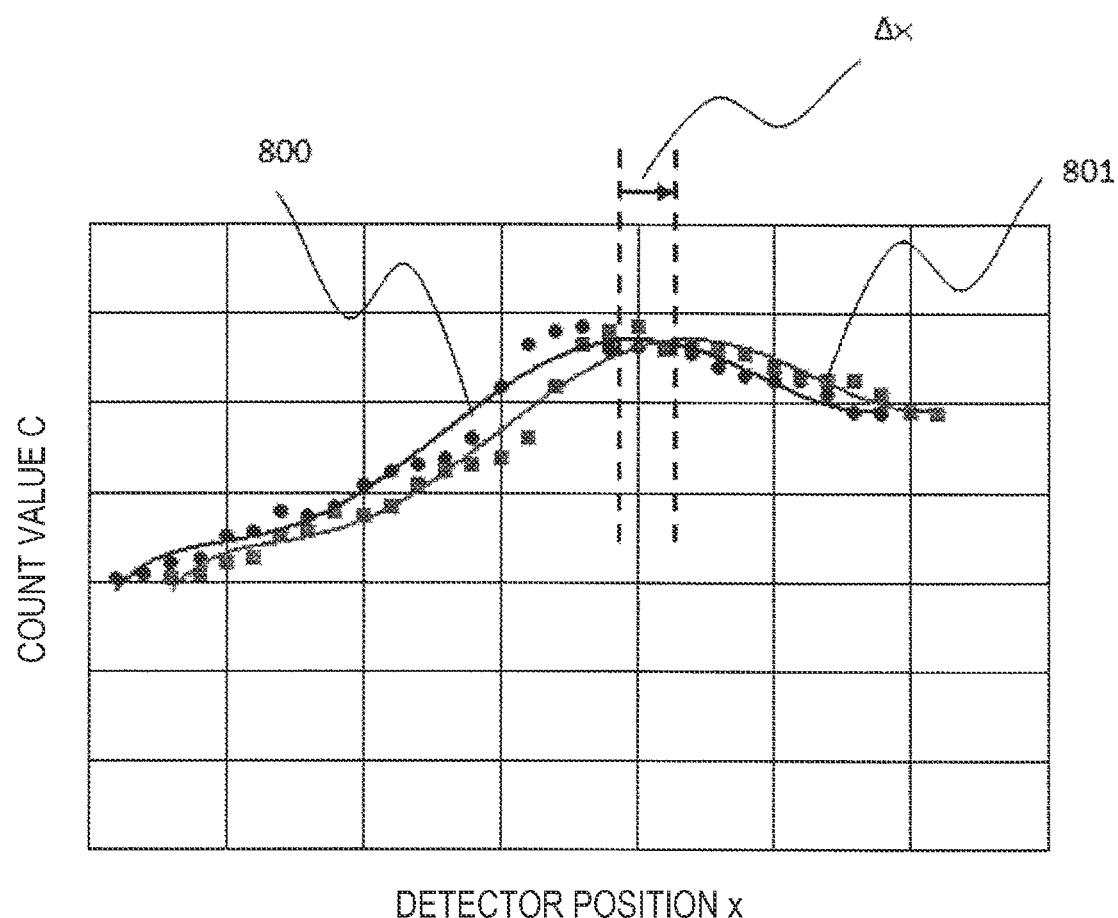
FIG. 8 is a diagram conceptually illustrating a method of obtaining an arrival position of a beam according to the second embodiment of the present invention.

FIG. 8 illustrates a count value distribution (base profile) 800 along the detector position of the gamma ray detector 30 obtained by simulation and a measured count value distribution (profile) 801. In this example, the difference ($\Delta x$) from the maximum value of the curve approximating the two profiles is calculated as the shift amount.

Although the distribution of the gamma rays at the beam irradiation axis shows a clear peak (BP) as illustrated in FIG. 2, a sharp peak does not appear in the profile of the count value of the gamma ray detector 30, but the shift amount can be accurately calculated by using an appropriate feature point. Further, according to the present embodiment, similarly to the first embodiment, by using the shield having the plurality of transmission portions (slits), it is possible to monitor the beam arrival position in a wide range without lowering accuracy.

Third Embodiment

In the present embodiment, a plurality of pieces of reference data having different irradiation target positions are prepared, and the actual beam arrival position is determined by matching these pieces of reference data with the actually measured data. Therefore, as illustrated in FIG. 3(C), a calculation unit 51C of the present embodiment includes a correlation calculation unit 517.

Figure 9:
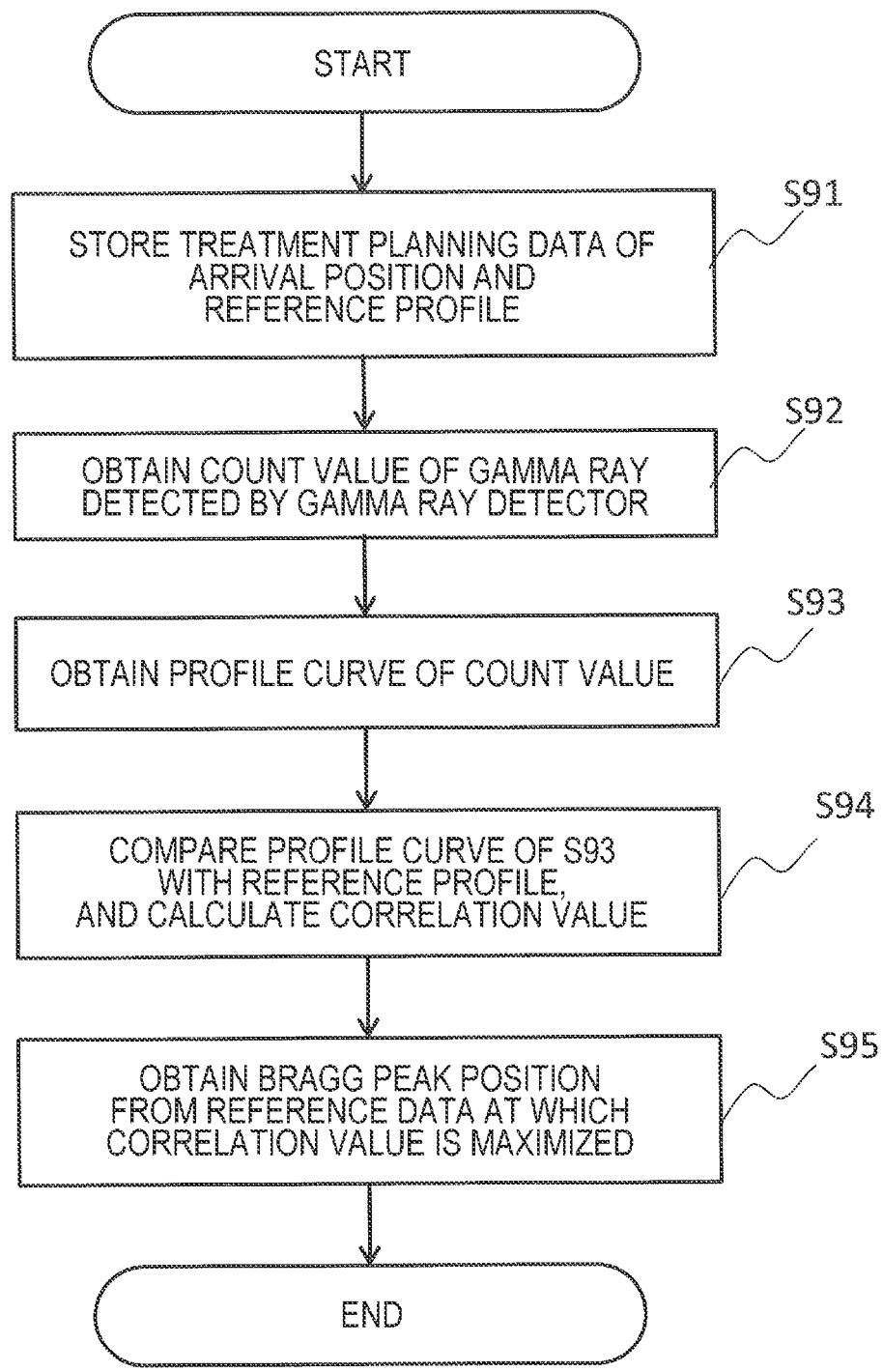
FIG. 9 is a flowchart of processing of obtaining an arrival position of a beam according to a third embodiment of the present invention.

Hereinafter, processing of the calculation unit 51C of the present embodiment will be described with reference to the flow of FIG. 9.

In the present embodiment, as reference data, a profile (reference profile) when the gamma ray detector 30 detects a gamma ray generated when each of a plurality of positions z1, z2, ... on the beam irradiation axis is irradiated with a charged particle beam by simulation is acquired, and a plurality of reference profiles having different arrival positions on the beam irradiation axis are stored in the DB 55 (S91).

Next, irradiation is performed a plurality of times on the target position of the actual irradiated object 20 according to the treatment planning by the particle irradiation apparatus 1, and at that time, the calculation unit 51C detects the generated gamma rays by the gamma ray detector 30 and obtains a count value (S92), and further, creates a profile of the count value using the obtained count value (S93).

The calculation unit 51C reads a plurality of pieces of reference data (reference profiles of count values) stored in the DB 55, and the correlation calculation unit 517 calculates a correlation between the profile curve created in Step S53 and the plurality of read profile curves (S94) and determines a profile curve having the maximum correlation among the reference data (S95). The beam arrival position when the determined reference data is created is set as an actual irradiation position (BP).

When the correlation values of two pieces of reference data having adjacent beam arrival positions are substantially the same, an intermediate position between the beam arrival positions of these two pieces of reference data may be determined as the actual irradiation position.

Although the case where the reference data is the profile of the count value and the profiles of the count values are compared has been described above, a reconfiguration profile (reference reconfiguration profile) obtained by converting the profile of the count value into a profile along the beam irradiation axis may be used as the reference data. In this case, similarly to the first embodiment, the profile of the count value obtained when the particle beam irradiation is performed on the irradiated object a plurality of times is reconfigured to the profile on the beam irradiation axis using the geometric relationship between the slit 41 of the shield 40 and the position on the beam irradiation axis and the detector position of the gamma ray detector, and the correlation with the reference data calculated by setting different beam arrival positions is calculated.

According to the present embodiment, it is possible to accurately estimate the arrival position by preparing a plurality of pieces of reference data in advance. Other effects are the same as those of the above-described embodiment.

Embodiment of Structure

Although the embodiment of the function of the control apparatus (particularly, the calculation unit 51) has been described based on the beam monitoring system 3 illustrated in FIG. 1, the structure of the beam monitoring system 3 is not limited to that of FIG. 1, and various modifications can be made. Hereinafter, modifications of the structure will be exemplified.

<First Modification>

Figure 10:
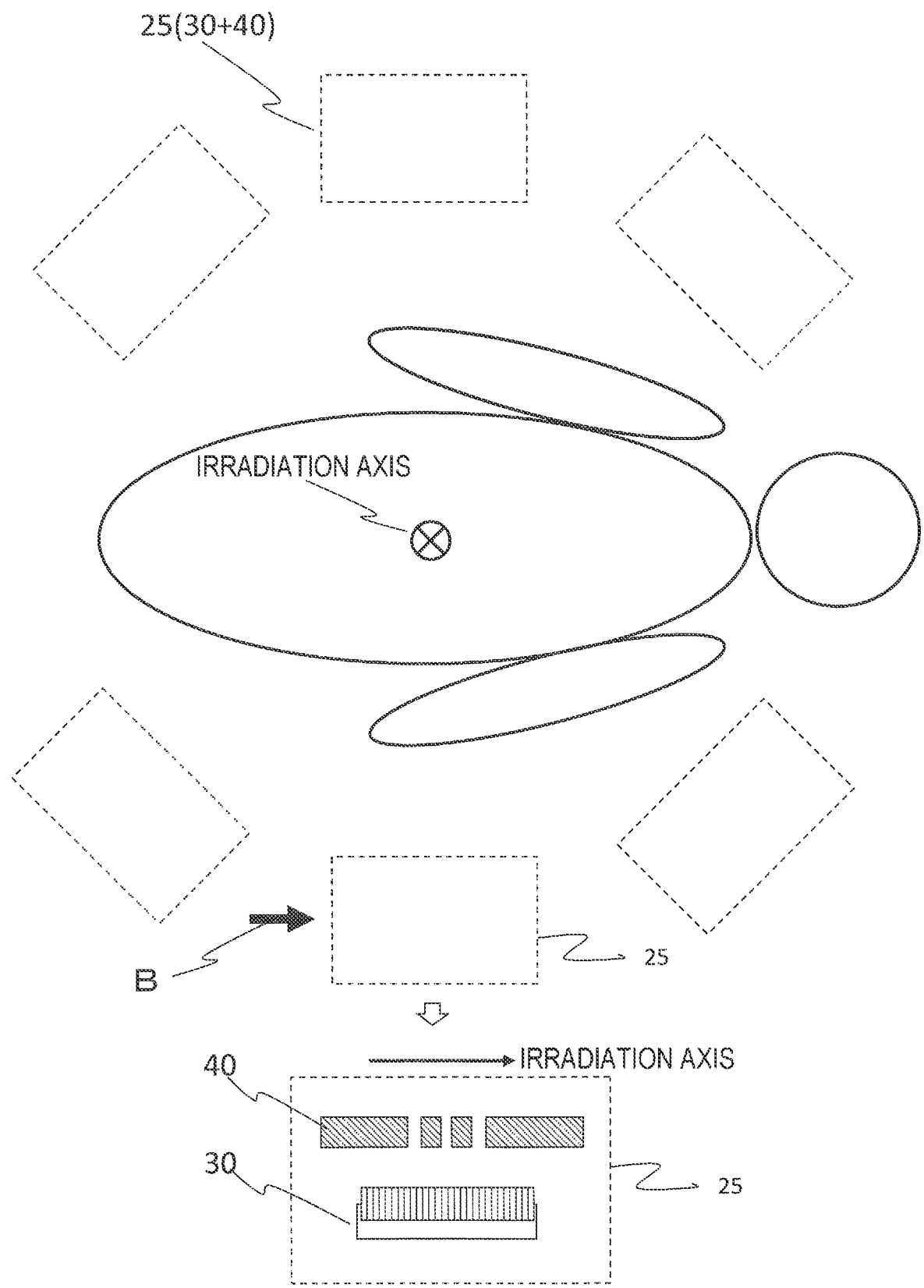
FIG. 10 is a diagram illustrating a modification of the shield structure.

FIG. 1 illustrates a case where the beam monitoring system 3 includes one gamma ray detector 30. However, the number of gamma ray detectors 30 may be two or more. By installing a plurality of gamma ray detectors 30, accuracy of gamma ray detection is improved, and accuracy of calculating BP and accuracy of calculating a beam arrival position can be improved. FIG. 10 illustrates an example of a beam monitoring system in which six gamma ray detectors 30 are disposed around the beam irradiation axis.

In FIG. 10, the beam irradiation axis 11A is vertical to the paper surface, and six detection units 25 are disposed around the beam irradiation axis so as to surround the patient as the irradiated object 20. The six detection units 25 are connected to one control apparatus 50 (FIG. 1). The detection unit 25 is an assembly (assembly) in which the gamma ray detector 30 and the shield 40 are fixed at a predetermined interval such that the arrangement direction of the detection elements and the arrangement direction of the slits 41 are parallel.

Each of the detection units 25 is disposed around the beam irradiation axis 11A such that the arrangement direction of the detection elements is parallel to the beam irradiation axis. That is, when the detection unit 25 is viewed from the viewpoint indicated by the thick arrow B in the drawing, as illustrated in the lower diagram of FIG. 10, the shield 40 is disposed such that the gamma ray detector 30 is on the outer side on the beam irradiation axis side, and the axial direction and the detection element arrangement direction coincide with each other. The distance between the detection unit 25 and the beam irradiation axis may be the same or different in each detection unit 25, but when a reconfiguration profile is created from the profile of the count value of the gamma rays, information of each distance is given to the control apparatus 50.

Also in the beam monitoring system 3 of the present modification, the control apparatus 50 detects the gamma rays generated by the particle beam irradiation and estimates the beam arrival distance (BP) using the detection result, which is similar to the above-described embodiment, and the method of estimating the beam arrival distance may be a method of any embodiment. However, in the present embodiment, the calculation unit 51 of the control apparatus 50 inputs detection results from the six gamma ray detectors 30, calculates respective count values, and creates a profile. At that time, the calculation unit 51 may obtain a profile by adding the count values of the six devices, or may create each profile and then combine or average the profiles.

Thereafter, calculating the arrival position using the base data or the reference data, displaying the calculated arrival position on the display unit 53, and performing control to stop the particle irradiation apparatus 1 as necessary are similar to the above-described embodiments.

Note that FIG. 10 illustrates an example in which six detection units 25 are disposed, but the number of detection units 25 is arbitrary, and the detection units 25 can be appropriately disposed in consideration of the positional relationship with the irradiation site and the irradiated object. For example, FIG. 10 illustrates a case where the particle beam is emitted from the upper side or the lower side of the abdomen of the patient laid upward or downward, but for example, in a case where the head is irradiated with the particle beam, two or three detection units 25 may be disposed with the irradiation axis interposed therebetween.

According to the present modification, the estimation accuracy of the beam arrival position can be further improved by increasing the number of detection units 25.

<Second Modification>

As the gamma ray detector 30, it is also possible to adopt a structure in which detectors are stacked in the thickness direction of the detection element. An example is illustrated in FIG. 11.

Figure 11:
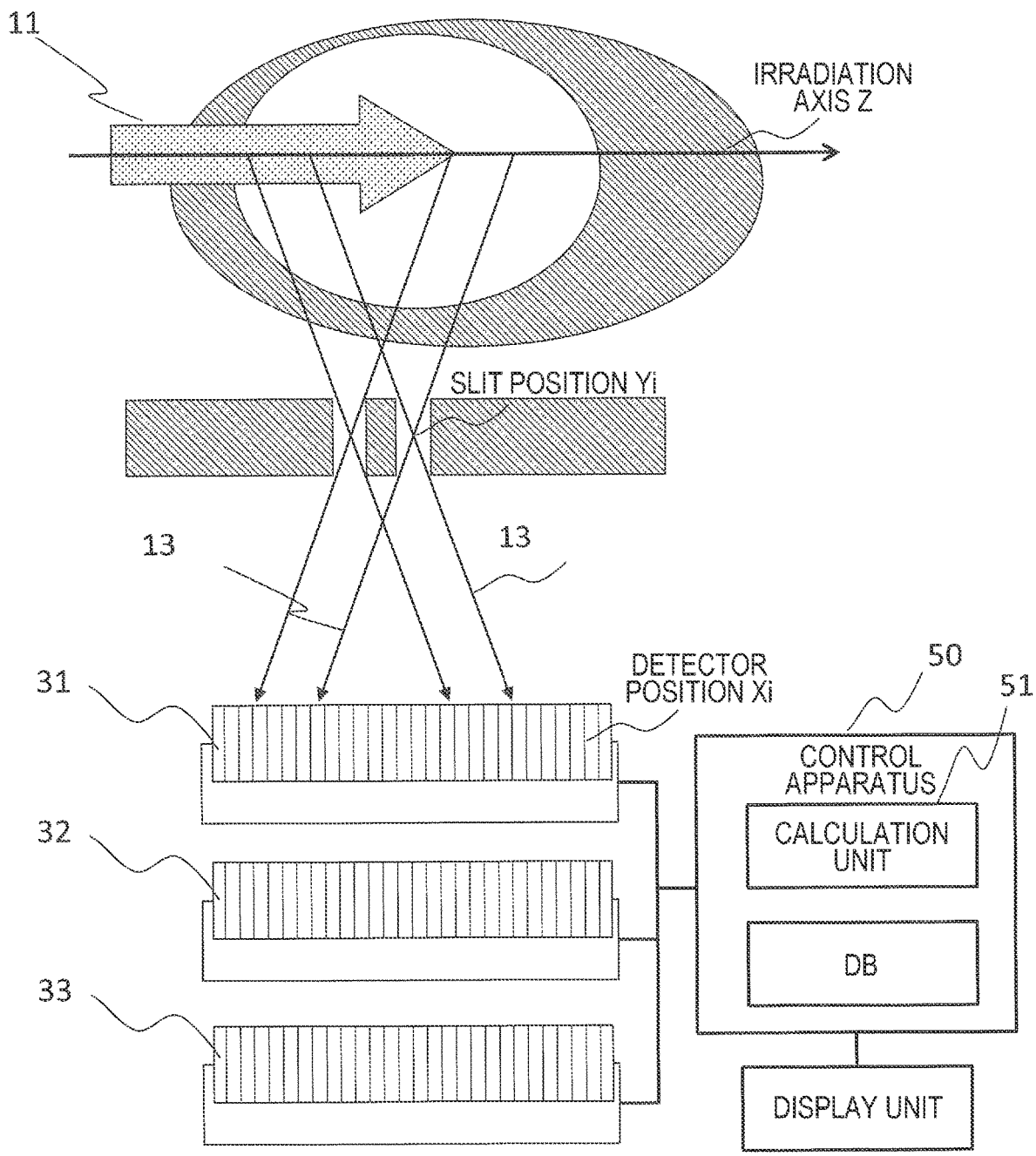
FIG. 11 is a diagram illustrating a modification of a detector structure.

The gamma ray detector 30 illustrated in FIG. 11 has a structure in which three detectors 31, 32, and 33 are stacked. Not all the gamma rays generated when the particle beam passes through the irradiated object and arriving at the gamma ray detector 30 are captured by the gamma ray detector 30, and some of the gamma rays are transmitted through. Although it is possible to increase the capture rate by increasing the thickness of the scintillator constituting the detector, in that case, the accuracy in the flight direction decreases, and the relationship between the position on the beam irradiation axis and the detector position becomes unclear.

In the present modification, the detectors are stacked without increasing the thickness of the scintillator, thereby increasing the gamma ray detection sensitivity. The detection results of the detectors 31 to 33 are integrated into one control apparatus 50, and the arrival position is calculated as in the first modification. As a result, also in the present embodiment, it is possible to improve the calculation accuracy by the addition effect of the detection results.

The structure of the detector of the present modification can also be employed in each detector of the first modification in which a plurality of gamma ray detectors are installed.

<Third Modification>

Figure 12:
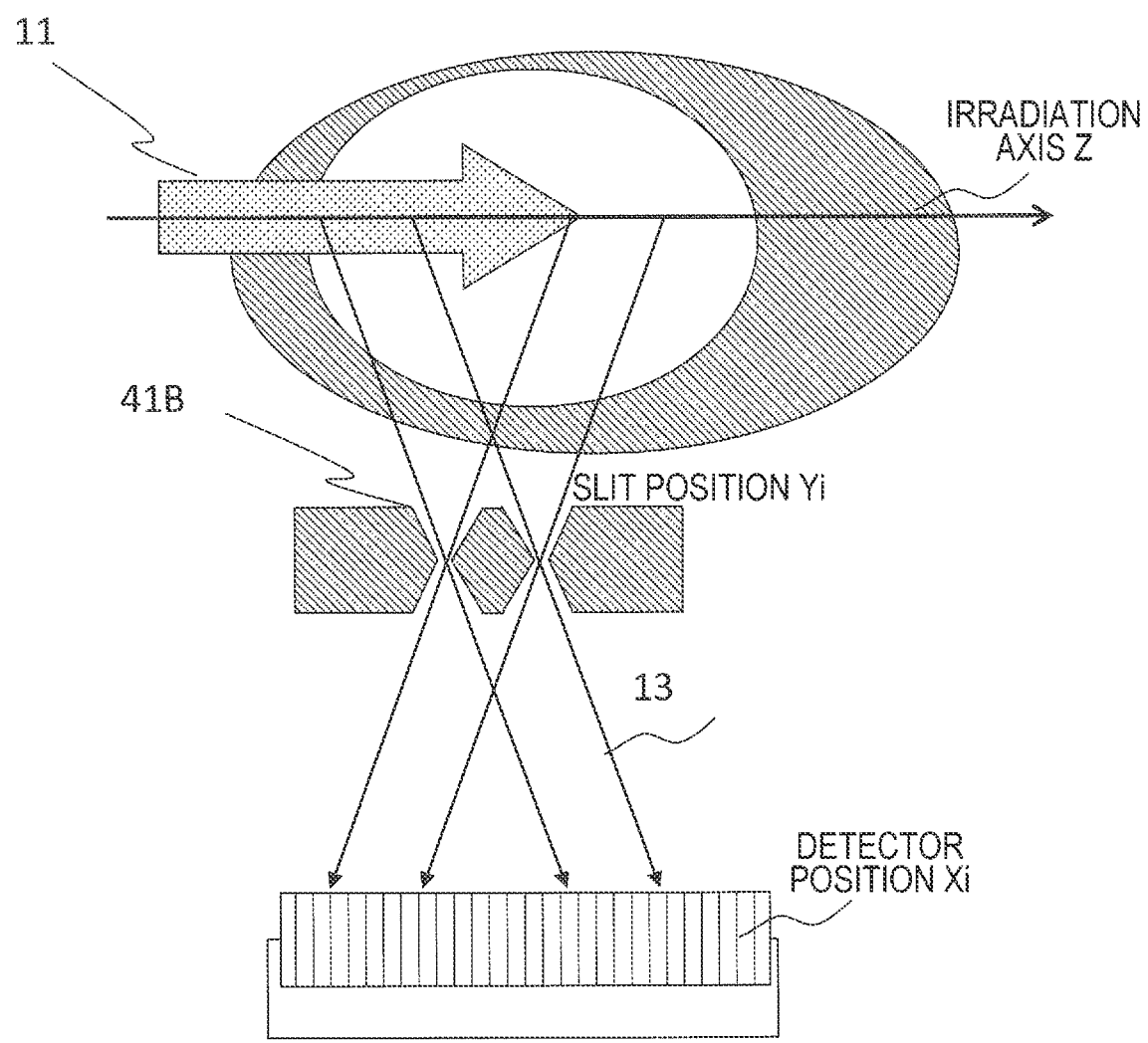
FIG. 12 is a diagram illustrating a modification of a slit structure.

FIG. 1 illustrates the case where the shape of the cross section including the irradiation axis is rectangular as the shape of the slit 41 of the shield 40. However, the shape of the slit 41 is not limited to the rectangular shape, and may be, for example, a shape in which the width changes in the thickness direction of the shield 40 as illustrated in FIG. 12. The slit 41 illustrated in FIG. 12 has a cross-sectional shape in which the width is the narrowest at the center in the thickness direction and the width increases from the center toward the end.

With such a cross-sectional shape, the correspondence between the position on the irradiation axis and the detector position is limited as compared with the rectangular slit, so that the detection sensitivity can be increased. In addition, if the width at the center is the same as the width of the rectangular slit, the range detected by one slit can be expanded, and the sensitivity in the axial direction can be improved.

The first to third modifications can be applied to the above-described first to third embodiments alone or in appropriate combination.

Although some embodiments and modifications of the present invention have been described above, these embodiments have been presented as examples, and are not intended to limit the scope of the invention. These novel embodiments can be implemented in various other forms, and various omissions, substitutions, and changes can be made without departing from the gist of the invention. The accompanying claims and their equivalents are intended to cover such embodiments or modifications as would fall within the scope and spirit of the invention.

REFERENCE SIGNS LIST

1 particle irradiation apparatus
3 beam monitoring apparatus (beam monitoring system)
11 particle beam
13 gamma ray
10 irradiation control apparatus
20 irradiated object (patient)
25 assembly of detector and shield (detection unit)
30 gamma ray detector
31 to 33 detector
40 shield
41 slit (transmission portion)
50 control apparatus
51, 51A, 51B, 51C calculation unit
53 display unit
55 database (DB)
100 particle therapy system

The invention claimed is:

1. A beam monitoring system that detects an immediate gamma ray generated along an irradiation axis of a particle beam with which an irradiated object is irradiated and monitors an arrival position of the particle beam, the beam monitoring system comprising:
 a detector unit including a plurality of detectors arranged along a traveling direction of the particle beam and configured to detect gamma rays;

a gamma ray shield disposed between an irradiation axis of the particle beam and the detector unit and formed with a plurality of transmission portions along the irradiation axis configured to transmit gamma rays; and a central processing unit (CPU) configured to:

integrate a count value of gamma rays injected at different times through the plurality of transmission portions into one detector, create a profile obtained by plotting integrated values of gamma ray count values for each of the respective detectors, separate the profile of the gamma ray count values for each of the respective detectors into a plurality of profiles for each of the transmission portions, convert the profiles for each of the transmission portions into a gamma ray count value along the irradiation axis to create a reconfiguration profile, and estimate a Bragg peak at which energy of the particle beam is maximized using the reconfiguration profile.

2. The beam monitoring system according to claim 1, wherein the CPU is configured to calculate a position on the irradiation axis based on a geometric relationship among the transmission portion, a detector, among the detectors, and the irradiation axis using the gamma ray count value for each transmission portion, and obtain a gamma ray count value generated at the position.

3. The beam monitoring system according to claim 2, wherein the CPU is configured to:

calculate a ratio of a count value from each transmission portion in the integrated value of the gamma ray count values in advance using base data obtained by performing measurement or simulation under a condition that gamma rays are transmitted through only a single transmission portion for each of a plurality of transmission portions, and separate the profile of the gamma ray count values by using the ratio.

4. The beam monitoring system according to claim 3, wherein the CPU is configured to:

calculate a ratio of a count value from each transmission portion in the integrated value of the gamma ray count value in advance using base data obtained by simulating a count value of gamma rays injected on the respective detectors for the particle beam assuming a predetermined arrival position, and separate the profile of the gamma ray count values by using the ratio.

5. The beam monitoring system according to claim 1, wherein a plurality of sets of the gamma ray shields and the detectors are disposed around the irradiation axis, and wherein the CPU is configured to estimate the Bragg peak using detection results of the plurality of sets.

6. The beam monitoring system according to claim 1, wherein the transmission portion is a slit formed in the gamma ray shield.

7. The beam monitoring system according to claim 6, wherein the slit has a slit width gradually decreasing toward a center in a thickness direction of the gamma ray shield in a cross section including the irradiation axis.

8. The beam monitoring system according to claim 1, wherein the plurality of detectors are stacked in a direction orthogonal to an arrangement direction of the detection elements.

9. The beam monitoring system according to claim 1, wherein the CPU is configured to:

extract in advance features of a base profile obtained by simulating a count value of gamma rays injected on the respective detectors and a profile obtained by actual measurement for a particle beam assuming an arrival position, and estimate a Bragg peak of a particle beam to be monitored from a difference between a position of a feature of the base profile and a position of a feature of the profile obtained by the actual measurement.

10. The beam monitoring system according to claim 1, further comprising:

a storage that stores in advance a plurality of reference profiles obtained by simulating a count value of gamma rays injected on the respective detectors or a reference reconfiguration profile obtained by converting the reference profile into a gamma ray count value along the irradiation axis for a plurality of particle beams assuming a plurality of different arrival positions, wherein the CPU is configured to estimate a Bragg peak for a particle beam to be monitored based on a matching degree between a profile created for the particle beam to be monitored and the reference profile or a matching degree between a reconfiguration profile of the profile and the reference reconfiguration profile.

11. A particle therapy system comprising:

a particle beam generator that generates a particle beam;

a particle beam controller that controls the particle beam generator; and a beam monitoring apparatus that is disposed at least at one location around an irradiated object irradiated with the particle beam and monitors a range of the beam, wherein the beam monitoring apparatus is the beam monitoring system according to claim 1.

12. The particle therapy system according to claim 11, wherein the particle beam control apparatus inputs a result of a Bragg peak estimated by the beam monitoring apparatus, and stops generation of a particle beam by the particle beam generator when a difference between a beam arrival position determined based on the estimated Bragg peak and a planned arrival position is a predetermined value or more.

13. A beam monitoring method for detecting an immediate gamma ray generated along an irradiation axis of a particle beam with which an irradiated object is irradiated and monitoring a range of the particle beam, the beam monitoring method comprising:

disposing a detector unit including a plurality of detectors that detect gamma rays in a vicinity of the irradiated object such that an arrangement direction of the detection elements substantially coincides with the irradiation axis, and disposing a gamma ray shield in which a plurality of transmission portions that transmit the gamma rays are formed along the irradiation axis, between the particle beam and the detector unit;

integrating, when the particle beam passes through the irradiated object, count values of gamma rays injected on individual detectors at different times through the plurality of transmission portions;

creating a profile in which an integrated value of gamma ray count values is plotted for each of the respective detectors;

separating the profile of the gamma ray count values for each of the respective detectors into a plurality of profiles for each of the transmission portions;

converting the profiles for each of the transmission portions into a gamma ray count value along the irradiation axis to create a reconfiguration profile; and estimating a Bragg point at which energy of the particle beam is maximized, using the reconfiguration profile.

* * * * *